US009532965B2

(12) United States Patent
Minatelli et al.

(10) Patent No.: US 9,532,965 B2
(45) Date of Patent: *Jan. 3, 2017

(54) **PLANT DERIVED SEED EXTRACT RICH IN ESSENTIALLY FATTY ACIDS DERIVED FROM *SALVIA HISPANICA* L. SEED: COMPOSITION OF MATTER, MANUFACTURING PROCESS AND USE**

(71) Applicant: U.S. NUTRACEUTICALS, LLC, Eustis, FL (US)

(72) Inventors: John A. Minatelli, Mount Dora, FL (US); W. Stephen Hill, Ocala, FL (US); Rudi E. Moerck, Sanford, FL (US); Uy Nguyen, Eustis, FL (US)

(73) Assignee: U.S. NUTRACEUTICALS, LLC, Eustis, FL (US)

( * ) Notice: Subject to any disclaimer, the term of this patent is extended or adjusted under 35 U.S.C. 154(b) by 208 days.

This patent is subject to a terminal disclaimer.

(21) Appl. No.: 14/038,907

(22) Filed: Sep. 27, 2013

(65) Prior Publication Data

US 2014/0023719 A1 Jan. 23, 2014

Related U.S. Application Data

(60) Continuation of application No. 13/206,757, filed on Aug. 10, 2011, now Pat. No. 8,574,637, which is a division of application No. 12/419,321, filed on Apr. 7, 2009, now Pat. No. 8,586,104.

(60) Provisional application No. 61/043,773, filed on Apr. 10, 2008.

(51) Int. Cl.
| | | |
|---|---|---|
| *A61K 36/537* | (2006.01) | |
| *A61K 36/185* | (2006.01) | |
| *A61K 31/202* | (2006.01) | |
| *A23D 9/00* | (2006.01) | |
| *C11B 1/06* | (2006.01) | |
| *C11B 1/10* | (2006.01) | |

(52) U.S. Cl.
CPC .............. *A61K 31/202* (2013.01); *A23D 9/00* (2013.01); *A23L 33/105* (2016.08); *A23L 33/115* (2016.08); *A23L 33/12* (2016.08); *A61K 36/537* (2013.01); *C11B 1/06* (2013.01); *C11B 1/104* (2013.01); *A61K 2236/15* (2013.01); *A61K 2236/37* (2013.01); *Y02P 20/544* (2015.11)

(58) Field of Classification Search
CPC ..... A61K 36/185; A61K 36/82; A61K 36/537
USPC ........................................ 424/725, 729, 746
See application file for complete search history.

(56) References Cited

U.S. PATENT DOCUMENTS

| | | |
|---|---|---|
| 5,332,803 A | 7/1994 | Miyazaki et al. |
| 5,585,400 A | 12/1996 | Cook et al. |
| 6,123,965 A | 9/2000 | Jacob et al. |
| 6,552,081 B1 | 4/2003 | Freedman et al. |
| 6,827,965 B1 | 12/2004 | Fitzpatrick |
| 7,959,950 B2 | 6/2011 | Evans et al. |
| 8,084,071 B2 | 12/2011 | Miyake et al. |
| 8,784,904 B2 | 7/2014 | Minatelli et al. |
| 9,114,142 B2 | 8/2015 | Minatelli et al. |
| 2002/0155182 A1 | 10/2002 | Belna |
| 2002/0168431 A1 | 11/2002 | Belna |
| 2003/0175403 A1 | 9/2003 | Gurin |
| 2004/0137132 A1 | 7/2004 | Nunez et al. |
| 2004/0185129 A1 | 9/2004 | Vuksan |
| 2005/0260145 A1 | 11/2005 | Leigh et al. |
| 2006/0127505 A1 | 6/2006 | Haines et al. |
| 2006/0147564 A1 | 7/2006 | Kim |
| 2007/0185340 A1 | 8/2007 | Van Toor et al. |
| 2007/0266774 A1 | 11/2007 | Gibson et al. |
| 2008/0095881 A1 | 4/2008 | Ber |
| 2008/0305096 A1 | 12/2008 | Verdegem et al. |
| 2008/0305190 A1 | 12/2008 | Vuksan |
| 2009/0048339 A1 | 2/2009 | Kanwar et al. |
| 2009/0181114 A1 | 7/2009 | Minatelli et al. |
| 2009/0181127 A1 | 7/2009 | Minatelli et al. |
| 2009/0258081 A1 | 10/2009 | Minatelli et al. |
| 2010/0144878 A1 | 6/2010 | Popp |
| 2010/0216885 A1 | 8/2010 | Kabaradjian |
| 2010/0260893 A1 | 10/2010 | Kabaradjian |
| 2010/0303999 A1 | 12/2010 | Chungu et al. |
| 2011/0293734 A1 | 12/2011 | Minatelli et al. |
| 2011/0306666 A1 | 12/2011 | Minatelli et al. |
| 2012/0027787 A1 | 2/2012 | Minatelli et al. |

FOREIGN PATENT DOCUMENTS

| | | |
|---|---|---|
| CN | 1369290 | 9/2002 |
| CN | 19125081 | 2/2007 |

(Continued)

OTHER PUBLICATIONS

Flavex Naturextrakte (CO2 extracts, Parfums Cosmetiques Actualities, 2007, 193, Feb./Mar. 2007, English Abstract, one page).*

(Continued)

*Primary Examiner* — Chris R Tate
*Assistant Examiner* — Randall Winston
(74) *Attorney, Agent, or Firm* — Allen, Dyer, Doppelt, Milbrath & Gilchrist, P.A.

(57) ABSTRACT

A *Salvia hispanica* L. derived seed oil extract composition of matter containing from 60-88% PUFAs in a ratio of from 3.1:1-3.3:1 of ALA to LA, 4-10% of C-18 mono-unsaturated fatty acid, 1-5% of C-18 saturated fatty acid and 4-8% of C-16 saturated fatty acid in a mixed triglyceride form stable at room temperature of 12-24 months containing a mixture of selected antioxidants.

12 Claims, No Drawings

(56) References Cited

FOREIGN PATENT DOCUMENTS

| DE | 10008948 | | 8/2001 |
|---|---|---|---|
| DE | 10008948 A1 | * | 8/2001 |
| EP | 0941672 | | 9/1999 |
| JP | 63190816 | | 8/1988 |
| JP | 63190816 A | * | 8/1988 |
| JP | 401056793 | | 3/1989 |
| WO | 99/62356 | | 12/1999 |
| WO | 02/072119 | | 9/2002 |
| WO | 2004/022725 | | 3/2004 |
| WO | 2009-126798 | | 10/2009 |
| WO | 2013/039537 | | 3/2013 |

OTHER PUBLICATIONS

The EFSA Journal (2005) 278, "Opinion of Scientific Panel on Dietetic Products, Nutrition and Allergies on a Request from the Commission Related to the Safety of Chia (*Salvia hispanica* L.) Seed and Ground Whole Chia Seed as a Novel Food Ingredient Intended for Use in Bread," http://www.efsa.eu.int/science/nda/nda_opinions/catindex_en.html, Oct. 5, 2005, pp. 1 12.

Laurange, "Agua Fresca De Chia" (Online) Aug. 30, 2007, XP002515363, Retrieved form the Internet: URL:http://www.saveurmexicaines.com/templates/home.php?page=86 content=128 &Ing=fr, 2 pages.

"Supercritical Chia Seed Oil Could Becoome Leading Source of Omega-3 Linolenic Acid" (Online) Nov. 30, 2005, XP002515364, Retrieved from the Internet: http://www.scientistilive.com/European-Food-Scientist/Ingredients/Supercritical_Chia_Seed_Oil_could_become_leading_source_of_omega-3_linolenic_acid/14463, 4 pages.

"Chia Samen C02-to Extrakt" (Online) Jul. 7, 2005, Rehlingen, De, Retrieved from the Internet: URL:http://www.flavex.com/hmd.html, 1 page.

"Valensa Introduces Tresalbio™ *Salvia hispanica* Seed CO2 Extract," Oct. 9, 2006, Retrieved from the Internet: http://www.usnutra.com/resources/news/Seed-CO2.php, 2 pages.

Coates et al., "Commercial Production of Chia in Northwestern Argentina," Journal of the American Oil Chemists' Society, vol. 75, No. 10, 1998, pp. 1417-1420.

"Valsena Launches O2B™ Peroxidation Blocker Technology at Vitafoods 2006," Jun. 8, 2006, Retrieved from the Internet: http://www.usnutra.com/resources/news/Technology-Vitafoods.php, 1 page.

Surette et al., "Inhibition of Leukotriene Synthesis, Pharmacokinetics, and Tolerability of a Novel Dietary Fatty Acid Formulation in Healthy Adult Subjects," Clinical Therapeutics, vol. 25, No. 3, Mar. 2003, pp. 948-971.

Reverchon et al., "Supercritical Fluid Extraction and Fractionation of Natural Matter," Journal of Supercritical Fluids, vol. 38, No. 2, Sep. 1, 2006, pp. 146-166.

Illes et al., "Extraction of Hiprose Fruit by Supercritical CO2 and Propane," Journal of Supercritical Fluids, vol. 10, No. 3, Aug. 1, 1997, pp. 209-218.

Catchpole et al, "Extraction of Seed Oils Using Supercritical CO2 and Subcritical Propane," Proceedings of the 2nd International Meeting on High Pressure, 2001, pp. 1-13.

Taga et al., "Chia Seeds as a Source of Natural Lipid Antioxidants," Journal of the American Oil Chemists' Society, 1984 Department of Foods and Nutrition, Purdue University, West Lafayette, Indiana, vol. 61, No. 5, May 1984, pp. 928-931.

List et al., "Oxidative Stability of Seed Oils Extracted with Supercritical Carbon Dioxide," Journal of the American Oil Chemists' Society, vol. 66, No. 1, Jan. 1, 1989, pp. 98-101.

Gomez et al., "Recovery of Grape Seed Oil by Liquid and Supercritical Carbon Dioxide Extraction: A Comparison with Conventional Solvent Extraction," Chemical Engineering Journal and the Biochemical Engineering Journal, vol. 61, No. 3, Mar. 1996, pp. 227-231.

Dunford et al., "Nutritional Components of Supercritical Carbon Dioxide Extracted Wheat Germ Oil," 6th Symposium on Supercritical Fluids, Retrieved from the Internet: http://www.ensic.inpl-nancy.fr/ISASF/Docs/Versailles/Papers/PN37.pdf, Apr. 2003, 6 pages.

Viable Herbal Solutions (www.web.archive.org/wev/200001241342/http:/viable-herbal.com/herbology 1/herbs42htm, Copyrighted 1996, 1997, 1998, and 2000), pp. 1-3.

Flavex Naturextrackt (CO2 Extract, Parfums Cosmetiques Actualities, 2007, 193, Feb./Mar. 2007.

U.S. Appl. No. 13/910,577, filed Jun. 5, 2013.
U.S. Appl. No. 14/053,676, filed Oct. 15, 2013.
U.S. Appl. No. 13/853,805, filed Jul. 30, 2013.
U.S. Appl. No. 131960,847, filed Aug. 7, 2013.

"Deep extract supercritical CO2 extraction", May 2009, pgs. 1-3 0.

"Stabilization-O2B peroxidation blocker system", Sep. 2011, pp. 1-3.

"Defatting technology", Sep. 2011, pp. 1-2.

"Extraction technology—the case for supercritical CO2", Sep. 2011, pp. 1-4.

"Peritla seed oil—supercritical CO2 extract", May 2012, pp. 1-4.

Kim et al. "Supercritical carbon dioxide extraction of penile seed oil", Foods and Biotechnology, Korean Society of Food Science and Technology, vol. 5, No. 4, Jan. 1996, pp. 300-304.

Database WPI, Week 200676, Thomson Scientific, Apr. 2006, 1 pg.

Database WPI, Week 200712, Thomson Scientific, Sep. 2006, pp. 1-2.

Database GNPD, Mintel, "Slimming Tea", Apr. 2013, pp. 1-4.

Database GNPD, Mintel, "Yonsei Milk: Omega-3 Perilla Soy Milk", May 2012, pp. 1-4.

"Valensa Launches Broad New Portfolio of Perilla-based Formulations", Press Release, Mar. 2013, pp. 1-4.

Kim et al., "Supercritical carbon dioxide extraction of perilla seed oil" Korean Society of Food Science and Technology, vol. 5, No. 4, 1996, pp. 300-304.

Cho et al., "Effects of defatted safflower and perilla seed powders on lipid metabolism in ovariectomized female rats fed high cholesterol diets", Journal of the Korean Society of Food Science and Nutrition, vol. 30, No. 1, Feb. 2001, pp. 1-2.

"Perilla oil, a source of heart-healthy alpha-linolenic acid", Life Extension Magazine, Apr. 2004, pp. 1-4.

Asif, "Health effects of omega-3,6,9 fatty acids: perilla frutescens is a good example of plant oils", Oriental Pharmacy and Experimental Medicine, vol. 11, No. 1, Mar. 2011, pp. 1-9.

Asif et al., "Nutritional and functional characterisations of perilla frutescens seed oil and evaluation of its effect on gastrointestinal motility", Malaysian Journal of Pharmaceutical Sciences, 2010, pp. 1-12.

Shin et al., "Lipid Composition of Perilla Seed," Journal of the American Oil Chemists, vol. 71, No. 6, Jan. 1994, pp. 619-622.

Przybylski, "Flax Oil and High Linelenic Oils," Bailey's Industrial Oil and Fat Products, Jan. 2005, pp. 281-301.

Database GNPD, "Entrox Dietary Supplement," Aug. 2001, p. 1.

* cited by examiner

PLANT DERIVED SEED EXTRACT RICH IN ESSENTIALLY FATTY ACIDS DERIVED FROM SALVIA HISPANICA L. SEED: COMPOSITION OF MATTER, MANUFACTURING PROCESS AND USE

RELATED APPLICATION(S)

This application is a continuation application of Ser. No. 13/206,757 filed Aug. 10, 2011, which is a divisional application of Ser. No. 12/419,321 filed Apr. 7, 2009, which is based upon prior filed provisional application Ser. No. 61/043,773 filed Apr. 10, 2008, the disclosures of which are incorporated by reference in their entirety.

FIELD OF THE INVENTION

This invention relates to plant-derived seed extracts and methods of making same.

BACKGROUND OF THE INVENTION

It is well known in the literature that Polyunsaturated Fatty Acids (PUFAs) of all types are highly susceptible to peroxide, free radical and light induced degradation including rancification and polymerization making them unsuitable for human consumption. For example, it is well known that flax seed oil, also known as linseed oil, readily undergoes free radical oxidation to advantageously form polymeric surfaces including oil based paints, hard furniture finishes and linoleum flooring. In addition, many companies offer flax seed oil for human consumption as a dietary supplement or food ingredient because of the high levels of PUFAs found in raw flax seed and its expeller pressed oils and more particularly Alpha-Linolenic Acid (ALA) and Linolenic Acid (LA). Many flax seed oil product labels suggest that the product must be refrigerated at all times due to the instability of such PUFAs in flax seed oil. Careful examination of the majority of commercially available flax seed oils obtained by expeller pressing, including those typically stored under refrigerated conditions, unfortunately reveals that they are unfit for human use based on their measured Peroxide Values (PVs). Such PV values above 3 meq/Kg (milliequivalents/gram) are deemed not suitable for salad oil applications and PV values above 10 meq/Kg are deemed to be unsuitable for human use because the measured PV value may be an early indicator of rancidity and free radical induced degradation. On the other hand, PV values taken alone do not adequately characterize such oils since a low PV value can also be associated with PUFA's that have already gone through the rancification process. Typical testing has revealed flax seed oil products sold for human consumption with observed PV's as high as 130 meq/kg also characterized with the odor associated with short chain aldehydes that make such oils "rancid" to olefactory senses.

In fact, most raw seed based oils in common cooking and baking use, such as soybean, corn and canola seed oils naturally contain enough PUFAs making them unsuitable, without further processing, for use as cooking oils. Therefore unless such PUFA containing raw seed oils are hydrogenated to fully saturated triglycerides using hydrogen and a catalyst prior to their use in cooking applications, they are considered to be unfit for use as cooking oils. These oils are typically first isolated by, for example, expeller pressing the appropriate seed, filtration of the crude seed oil to remove biomass and the resulting oil, containing significant levels of PUFAs, is then catalytically hydrogenated to reduce the PUFA content to levels suitable for use of the resulting oil in cooking applications. If the hydrogenation process is incomplete, however, the resulting mixtures are found to contain both undesirable heat labile PUFAs that quickly undergo rancification to small chain aldehydes in the resulting heated cooking oil as well as unsaturated trans-fatty acids which are believed to be detrimental to animal and especially human health.

Therefore, those skilled in the art will recognize the great difficulty in producing a shelf stable PUFA mixture wherein the PUFA content is as high as 70% wt/wt of the resulting seed extract from a natural seed source that then exhibits extraordinary room temperature stability.

SUMMARY OF THE INVENTION

In accordance with a non-limiting aspect, a composition of matter includes a supercritical $CO_2$ Salvia hispanica L. derived seed oil comprising from 60-88% PUFAs in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and comprising a mixture of selected antioxidants.

In another aspect, the composition of matter includes dietary supplement ingredients such as docosahexaenoic acid (DHA) and/or eicosapentaenoic acid (EPA) in pectin or gelatin based confectionary dietary supplement delivery systems. EPA, DHA, docosahexaenoic acid (DPA) or gamma-linlolenic acid (GLA), fish oil, krill oil, krill oil concentrate, borage oil, evening primrose oil, olive oil or other plant, animal or algal based seed or fruit oils are admixed therein either alone or in combination. Lipophilic antioxidants are added either alone or in combination with a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ).

In yet another aspect a hydrophilic antioxidant or sequesterant includes hydrophilic phenolic antioxidants including at least one of grape seed extract, tea extracts, ascorbic acid, citric acid, tartaric acid, and malic acid.

A method of manufacturing and method of using the composition is also set forth.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In accordance with a non-limiting aspect, a room temperature, shelf stable mixture of an approximate 3.3:1 mixture of alpha-linolenic acid ("ALA", "Omega-3 polyunsaturated fatty acid" ("PUFA")) to linoleic acid ("LA", "Omega-6 PUFA) has been prepared in the presence of limited amounts of saturated and mono-unsaturated fatty acids as their mixed triglycerides by the use of either supercritical fluid $CO_2$ solvent extraction of pre-milled *Salvia hispanica* L. seed alone, and more particularly, supercritical fluid $CO_2$ solvent extraction in the presence of mixtures of hydrophilic and lipophilic antioxidants, or, by the use of a common organic solvent extraction such as hexane or by the use of expeller pressing techniques.

Such Omega-3 and Omega-6 PUFAs are well known as essential fatty acids in man and many animals, which are useful in humans and animals in promoting, for example, a heart healthy condition in man. It is also well known, however, that PUFAs are extremely susceptible to rapid, uncontrollable free radical mediated degradation.

A PUFA rich seed oil extract is prepared from *Salvia hispanica* L. seed which contains one of nature's most favorable seed based concentrations and ratios of the essential fatty acids and more specifically the essential fatty acids ALA and LA in a ratio of approximately 3.3:1 and more particularly a mixture of said ALA and LA that is stable at room temperature for long periods of time when appropriately treated with antioxidants either before, during or after, or any combination thereof, supercritical fluid extraction, hexane extraction or expeller pressing of the seeds.

Such oils are used either alone or advantageously in combination with other ingredients, for example, algae, plant or fish derived alpha-linolenic acid (ALA) or linoleic acid (LA) metabolites such as eicosapentaenoic acid (EPA), docosapentaenoic acid (DPA), gamma-linlolenic acid (GLA) or docosahexaenoic acid (DHA) or any combination thereof, incorporated into appropriate foods, beverages or dietary supplements for the prevention or mitigation of such diseases as cardiovascular disease, arthritis, pain, blood clotting, dry eyes and brain health.

Such disease mitigation has been associated with the competitive control of the LA metabolic cascade and the resulting metabolic cascade products from LA metabolism known commonly as eicosanoids, such as the series 2 and 3 prostaglandins and thromboxanes, the series 4 leucotrienes and lipoxins and the series 5 leuotrienes all of which are potent platelet aggregators and/or inhibitors, pro-inflammatories, vasodilators, bronchoconstrictors, or anti-asthmatics and the like.

The consumption of ALA has been shown to be a very effective competitive substrate of delta-6 desaturase, which is known to be the rate limiting enzymatic step in both ALA and LA metabolism to the metabolic products discussed above.

Attempted extraction of *Saliva hispanica* L. un-milled seed, using supercritical $CO_2$ even at extraordinarily high pressures of 1000 bar or hexane solvent at atmospheric pressures, yields very little, if any, seed oil, therefore the seed must be milled prior to extraction. The extent of the milling, as measured by particle size distribution, is advantageous to the extraction process in accordance with a non-limiting aspect since the higher the surface area, the higher will be the efficiency and completeness of the extraction process by either organic solvent based or supercritical fluid based processes. In addition, it is advantageous to mill the seed in a blanket of inert gas such as nitrogen to prevent per-oxidative processes from taking place that would otherwise be initiated in the presence of air or oxygen and light.

In one embodiment, *Salvia Hispanica* L. whole seed is either first commutated in a standard knife or hammer mill or more preferably roller milled, preferably under a cold nitrogen atmosphere, to produce cracked seed biomass. The biomass is preferably treated with one or more hydrophilic and/or lipophilic antioxidants by mixing the antioxidants to the resulting biomass. In another embodiment, the antioxidant may be advantageously added to the seed prior to or during the milling process or at the point of extraction without pre-blending said antioxidants evenly throughout the resulting biomass due to the nature of the extraction process. The biomass is then transferred to a supercritical fluid extraction unit for separation of the seed oil from the cracked or flake-rolled biomass.

Alternatively, the pre-prepared biomass can be transferred to a common hexane solvent extractor, or an expeller press for example, and the oil extracted from the biomass accordingly. Preferably either process is conducted in the absence of oxygen or air.

The supercritical fluid extraction of the milled seed admixed with hydrophilic and/or lipophilic antioxidants is accomplished by subjecting the pre-milled cracked or flake-rolled seed to supercritical $CO_2$, or $CO_2$ and propane as a co-solvent or supercritical propane alone at from 40-1000 bar at from 30-100 Deg. C. More preferably the seed oil is extracted from the biomass between 50-800 bar at 50-90 deg. C. in such $CO_2$ amounts measured in kgs/kg of biomass and for such times as may be required to extract large portions of the seed oil content from the biomass. In addition, entrainment solvents can be added to the supercritical fluid to further enhance the efficiently of such extractions. For example, supercritical carbon dioxide extraction of the biomass can be enhanced by the addition of propane to the supercritical extraction fluid.

The resulting seed oil dissolved in supercritical solvent(s) is next allowed to fractionate in two separate pressure step-down stages allowing the collection of a light and heavy fraction of seed oil extract. This light fraction also contains water that has been co-extracted from the seed mass. The resulting seed oil, after degassing, is separated from any water that may have been carried over during the extraction of the biomass containing said water. The light fraction of the seed oil extract is rich in taste and odor components and may be admixed with the heavy fraction or may be discarded depending on the desired product characteristics.

After separation of the water remaining in each fraction, the fractions are then held under nitrogen or other inert gas and additional amounts of lipophilic and/or hydrophilic antioxidants may then be added. In addition, the resulting fractions may also be treated with bleaching clay, carbon and such other processing aids as may be required to render the oil suitable for its intended use in humans and animals.

The PV of the resulting seed oil extract is typically under 2.0 meq/Km, while accelerated decomposition, using a Rancimat instrument, remarkably indicates an extrapolated room temperature shelf life of from 1-2 years. When the same process is repeated without the use of antioxidants, the resulting PV is surprisingly under 10.0 meq/Kg most probably due to the use of supercritical CO2 resulting in minimal exposure of the oil to oxygen species, however the resulting oil quickly begins to build peroxide value in the presence of air even when stored at temperatures of 0 Degs. C. In addition, such unstabilized oils, under accelerated rancimat testing exhibit very poor stability to heat and oxygen unlike the rancimat performance observed in stablizied oils derived from the process described above.

The resulting supercritical fluid seed oil extract of the invention contains from 60-88% PUFAs in a ratio of from 3.1:1-3.3:1 of ALA:LA, 4-10% of C18 mono-unsaturated fatty acid, 1-5% of C-18 saturated fatty acid and 4-8% C-16 saturated fatty acid composition in a mixed triglyceride form depending on the seed source employed.

On the other hand, if the process described above is conducted without the use of hydrophilic and/or lipophilic antioxidants, the resulting seed oil extract exhibits an initial low PV but accelerated stability testing using a Rancimat instrument indicates an extrapolated room temperature shelf stability of less than two months.

The stability of the resulting oil at room temperature that is manufactured without the use of added antioxidants cannot be easily explained because of the available levels of the powerful natural antioxidants found in Salvia hispanica L. whole seed whose activity can be easily measured in Oxygen Radical Absorbance Capacity (ORAC) units. Salvia hispanica L. has a measured ORAC number of 3000 micromoles TE ORAC units/gram of seed and is known to contain such antioxidants as myricetin, quercetin, kaempferol, caffeic acid, and chlorogenic acid. In addition, it is well known that the Salvia hispanica L. whole seed, unlike many other seeds bearing PUFA containing oil, exhibits a shelf life of at least 5 years due to its structure and the naturally occurring antioxidants available in the seed matrix.

In addition, cold pressing of Salvia hispanica L. whole seed also produces unstable seed oil without careful addition of appropriate antioxidants to the seed prior to the expeller pressing process.

In a non-limiting example the composition of matter is formed from a supercritical $CO_2$ derived Salvia hispanica L. derived seed oil comprising from 60-88% PUPAS in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and comprising a mixture of selected antioxidants.

It includes docosahexaenoic acid (DHA) and/or eicosapentaenoic acid (EPA) in pectin or gelatin based confectionary dietary supplement delivery systems and in another aspect EPA, DHA, docosapentaenoic acid (DPA) or gamma-linlonenic acid (GLA), fish oil, krill oil, krill oil concentrate, borage oil, evening primrose oil, olive oil or other plant, animal or algal based seed or fruit oils are admixed therein.

Lpophilic antioxidants are added either alone or in combination with a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ). The hydrophilic antioxidant or sequesterant includes hydrophilic phenolic antioxidants including at least one of grape seed extract, tea extracts, ascorbic acid, citric acid, tartaric acid, and malic acid in another aspect.

A method of manufacturing a Salvia hispanica L. derived seed oil in another non-limiting example is set forth. The seed oil comprises from 60-88% PUFAs in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and includes antioxidants. The method includes milling or roller press flaking Salvia hispanica L. seed in the absence of oxygen to obtain a desired particle size distribution with or without the addition of hydrophilic or lipophilic antioxidants during the particle sizing process. The resulting biomass is subjected to supercritical fluid $CO_2$ extraction in the presence of lipophilic and or hydrophilic antioxidants. Any resulting seed oil fractions are collected. The water is separated in each fraction.

Any resulting seed oil fractions can be treated with additional antioxidants to afford a desired room temperature stability. The extent of oil extraction can be controlled by particle size distribution of the milled or flaked seed. Propane can be added in mixture with supercritical $CO_2$ in the supercritical state as an extraction solvent. In yet another aspect solvent can be extracted using hexane extraction at or near atmospheric pressures and the resulting boiling point of hexane in the absence of oxygen, separating the resulting water from the oil/hexane mixture and removing the hexane solvent by distillation at or below atmospheric pressure in the absence of oxygen.

Lipophilic antioxidants can be added to increase the room temperature stability of the resulting oil. The lipophilic antioxidants can be added either alone or in combination with a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ). The resulting dewatered seed oil can be treated with bleaching clay or activated carbon.

Pre-milled or roller press flaked seed can be treated with a lipophilic or hydrophilic antioxidant(s) prior to solvent extraction. The hydrophilic antioxidant or sequesterant can be formed from hydrophilic phenolic antioxidants including at least one of grape seed extract, tea extracts, ascorbic acid, citric acid, tartaric acid, and malic acid.

A method of mitigating or preventing cardiovascular disease, arthritic pain and inflammation, platelet aggregation, or treating dry eye syndrome, pre-menstrual symptoms or modifying immune response in humans or animals is set forth by applying an effective amount of a dietary supplement, food or beverage to which has been a composition mixed therewith and comprising a Salvia hispanica L. derived seed oil comprising from 60-88% PUFAs in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and includes antioxidants.

In one aspect, an emulsifying agent is added. In another aspect, nano- and/or micro-particles of rice or sugarcane based polycosanol are dispersed for enhancing a heart healthy dietary supplement. A stabilized oil in a fruit juice concentrate, fruit puree or other water based flavoring is dispersed in the presence of maltodextrin, or other carbohydrates, and a suitable emulsifying or emulsion stabilization agent that is vacuum spray dried to form an amorphous or crystalline solid suitable for use as a flavoring ingredient carrying stabilized PUFAs in flavored dietary supplements, foods and beverages. In yet another aspect, oil based flavors and fragrances suitable for use as an ingredient in foods, beverages and cosmetics are added. ALA and LA are also added as essential fatty acids.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

That which is claimed is:

1. A composition of matter comprising a supercritical $CO_2$ fluid *Salvia hispanica* L. derived seed oil comprising from 60-88% PUFAs in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is shelf stable at room temperature for 12-24 months and comprising an effective amount of added lipophilic and/or hydrophilic antioxidant stabilizer as a preservative that extends the shelf life of the seed oil, wherein the *Salvia hispanica* L. derived seed oil is made by subjecting the *Salvia hispanica* L seed to supercritical fluid CO2 extraction to produce a seed oil extract; fractionating the resulting seed oil extract in separate pressure step-down stages for collecting light and heavy fractions of seed oil extract; and separating the heavy fraction from the light fraction to form the final seed oil from the heavy fraction.

2. The composition of matter according to claim 1, and further comprising docosahexaenoic acid (DHA) and/or eicosapentaenoic acid (EPA) in pectin or gelatin based confectionary dietary supplement delivery systems.

3. The composition of matter according to claim 1, and further comprising EPA, DHA, docosapentaenoic acid (DPA) or gamma-linlolenic acid (GLA), fish oil, krill oil, krill oil concentrate, borage oil, evening primrose oil, olive oil or other plant, animal or algal based seed or fruit oils admixed therein.

4. The composition of matter according to claim 1, and further comprising lipophilic antioxidants either alone or in combination with a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA), and i) Tertiary Butyl hydroquinone (TBHQ).

5. The composition of matter according to claim 1, and further comprising a hydrophilic antioxidant or sequesterant comprising hydrophilic phenolic antioxidants including at least one of grape seed extract, tea extracts, ascorbic acid, citric acid, tartaric acid, and malic acid.

6. The composition of matter according to claim 1, wherein a peroxide value of the seed oil is under 2.0 meq/Km.

7. A composition of matter comprising a supercritical $CO_2$ fluid *Salvia hispanica* L. derived seed oil comprising from 60-88% PUFAs in a ratio of from 3.1:1-3.3:1 of alpha-linolenic acid (ALA) to linoleic acid (LA), 4-10% of C-18 mono-unsaturated acid, 1-5% of C-18 saturated fatty acid and 4-8% of C-16 saturated fatty acid in a mixed triglyceride form that is shelf stable at room temperature for 12-24 months and comprising an effective amount of added lipophilic and/or hydrophilic antioxidant stabilizer as a preservative that extends the shelf life of the seed oil, wherein the *Salvia hispanica* L. derived seed oil is made by subjecting the *Salvia hispanica* L seed to supercritical fluid CO2 extraction to produce a seed oil extract; fractionating the resulting seed oil extract in separate pressure step-down stages for collecting light and heavy fractions of seed oil extract; and separating the heavy fraction from the light fraction to form the final seed oil from the heavy fraction.

8. The composition of matter according to claim 7, and further comprising docosahexaenoic acid (DHA) and/or eicosapentaenoic acid (EPA) in pectin or gelatin based confectionary dietary supplement delivery systems.

9. The composition of matter according to claim 7, and further comprising EPA, DHA, docosapentaenoic acid (DPA) or gamma-linlolenic acid (GLA), fish oil, krill oil, krill oil concentrate, borage oil, evening primrose oil, olive oil or other plant, animal or algal based seed or fruit oils admixed therein.

10. The composition of matter according to claim 7, and further comprising lipophilic antioxidants either alone or in combination with a) phenolic antioxidants including at least one of sage, oregano, and rosemary; b) tocopherol; c) tocotrienol(s); d) carotenoids including at least one of astaxanthin, lutein, and zeaxanthin; e) ascorbylacetate; f) ascorbylpalmitate; g) Butylated hydroxytolene (BHT); h) Docosapentaenoic Acid (BHA); or i) Tertiary Butyl hydroquinone (TBHQ).

11. The composition of matter according to claim 7, and further comprising a hydrophilic antioxidant or sequesterant comprising hydrophilic phenolic antioxidants including one of grape seed extract, tea extracts, ascorbic acid, citric acid, tartaric acid, and malic acid.

12. The composition of matter according to claim 7, wherein a peroxide value of the seed oil is under 2.0 meq/Km.

* * * * *

UNITED STATES PATENT AND TRADEMARK OFFICE
CERTIFICATE OF CORRECTION

PATENT NO. : 9,532,965 B2
APPLICATION NO. : 14/038907
DATED : January 3, 2017
INVENTOR(S) : Minatelli et al.

It is certified that error appears in the above-identified patent and that said Letters Patent is hereby corrected as shown below:

On the Title Page

Delete the title page and substitute the attached title page therefor

In the Claims

Column 8, Line 1-44:         Delete:
(Allowed Claims 7-12)        Claim 7-12

Signed and Sealed this
Eleventh Day of April, 2017

Michelle K. Lee
*Director of the United States Patent and Trademark Office*

(12) United States Patent
Minatelli et al.

(10) Patent No.: US 9,532,965 B2
(45) Date of Patent: *Jan. 3, 2017

(54) **PLANT DERIVED SEED EXTRACT RICH IN ESSENTIALLY FATTY ACIDS DERIVED FROM *SALVIA HISPANICA* L. SEED: COMPOSITION OF MATTER, MANUFACTURING PROCESS AND USE**

(71) Applicant: U.S. NUTRACEUTICALS, LLC, Eustis, FL (US)

(72) Inventors: John A. Minatelli, Mount Dora, FL (US); W. Stephen Hill, Ocala, FL (US); Rudi E. Moerck, Sanford, FL (US); Uy Nguyen, Eustis, FL (US)

(73) Assignee: U.S. NUTRACEUTICALS, LLC, Eustis, FL (US)

( * ) Notice: Subject to any disclaimer, the term of this patent is extended or adjusted under 35 U.S.C. 154(b) by 208 days.

This patent is subject to a terminal disclaimer.

(21) Appl. No.: 14/038,907

(22) Filed: Sep. 27, 2013

(65) Prior Publication Data
US 2014/0023719 A1 Jan. 23, 2014

Related U.S. Application Data

(60) Continuation of application No. 13/206,757, filed on Aug. 10, 2011, now Pat. No. 8,574,637, which is a division of application No. 12/419,321, filed on Apr. 7, 2009, now Pat. No. 8,586,104.

(60) Provisional application No. 61/043,773, filed on Apr. 10, 2008.

(51) Int. Cl.
| | | |
|---|---|---|
| A61K 36/537 | (2006.01) | |
| A61K 36/185 | (2006.01) | |
| A61K 31/202 | (2006.01) | |
| A23D 9/00 | (2006.01) | |
| C11B 1/06 | (2006.01) | |
| C11B 1/10 | (2006.01) | |

(52) U.S. Cl.
CPC .......... *A61K 31/202* (2013.01); *A23D 9/00* (2013.01); *A23L 33/105* (2016.08); *A23L 33/115* (2016.08); *A23L 33/12* (2016.08); *A61K 36/537* (2013.01); *C11B 1/06* (2013.01); *C11B 1/10* (2013.01); *A61K 2236/15* (2013.01); *A61K 2236/37* (2013.01); *Y02P 20/344* (2015.11)

(58) Field of Classification Search
CPC ...... A61K 36/185; A61K 36/82; A61K 36/537
USPC .......................................... 424/725, 729, 746
See application file for complete search history.

(56) References Cited

U.S. PATENT DOCUMENTS

| | | |
|---|---|---|
| 5,332,803 A | 7/1994 | Miyazaki et al. |
| 5,585,400 A | 12/1996 | Cook et al. |
| 6,123,965 A | 9/2000 | Jacob et al. |
| 6,552,081 B1 | 4/2003 | Freedman et al. |
| 6,827,965 B1 | 12/2004 | Fitzpatrick |
| 7,959,950 B2 | 6/2011 | Evans et al. |
| 8,084,071 B2 | 12/2011 | Miyake et al. |
| 8,784,904 B2 | 7/2014 | Minatelli et al. |
| 9,114,142 B2 | 8/2015 | Minatelli et al. |
| 2002/0155182 A1 | 10/2002 | Belna |
| 2002/0168431 A1 | 11/2002 | Belna |
| 2003/0175403 A1 | 9/2003 | Gusin |
| 2004/0137132 A1 | 7/2004 | Nunez et al. |
| 2004/0185139 A1 | 9/2004 | Vuksan |
| 2005/0260145 A1 | 11/2005 | Leigh et al. |
| 2006/0127505 A1 | 6/2006 | Haines et al. |
| 2006/0147564 A1 | 7/2006 | Kim |
| 2007/0185340 A1 | 8/2007 | Van Toor et al. |
| 2007/0266774 A1 | 11/2007 | Gibson et al. |
| 2008/0095881 A1 | 4/2008 | Ber |
| 2008/0303096 A1 | 12/2008 | Verdegem et al. |
| 2008/0305190 A1 | 12/2008 | Vuksan |
| 2009/0048339 A1 | 2/2009 | Kanwar et al. |
| 2009/0181114 A1 | 7/2009 | Minatelli et al. |
| 2009/0181127 A1 | 7/2009 | Minatelli et al. |
| 2009/0258081 A1 | 10/2009 | Minatelli et al. |
| 2010/0144878 A1 | 6/2010 | Popp |
| 2010/0210865 A1 | 8/2010 | Kaliaradjian |
| 2010/0260883 A1 | 10/2010 | Kaliaradjian |
| 2010/0303999 A1 | 12/2010 | Chinnga et al. |
| 2011/0293734 A1 | 12/2011 | Minatelli et al. |
| 2011/0305666 A1 | 12/2011 | Minatelli et al. |
| 2012/0027787 A1 | 2/2012 | Minatelli et al. |

FOREIGN PATENT DOCUMENTS

| | | |
|---|---|---|
| CN | 1369299 | 9/2002 |
| CN | 1912508 | 2/2007 |

(Continued)

OTHER PUBLICATIONS

Flavex Naturextrakte (CO2 extracts, Parfums Cosmetiques Actualites, 2007, 193, Feb./Mar. 2007, English Abstract, one page).*

(Continued)

*Primary Examiner* — Chris R Tate
*Assistant Examiner* — Randall Winston
(74) *Attorney, Agent, or Firm* — Allen, Dyer, Doppelt, Milbrath & Gilchrist, P.A.

(57) ABSTRACT

A *Salvia hispanica* L. derived seed oil extract composition of matter containing from 60-88% PUFAs in a ratio of from 3.1:1-3.3:1 of ALA to LA, 4-10% of C-18 mono-unsaturated fatty acid, 1-5% of C-18 saturated fatty acid and 4-8% of C-16 saturated fatty acid in a mixed triglyceride form stable at room temperature of 12-24 months containing a mixture of selected antioxidants.

6 Claims, No Drawings